(12) United States Patent
Fries et al.

(10) Patent No.: US 11,141,112 B2
(45) Date of Patent: Oct. 12, 2021

(54) SET FOR APPLYING A FLAT, FLEXIBLE TWO-DIMENSIONAL THIN-FILM STRIP INTO LIVING TISSUE

(71) Applicant: Ernst Strüngmann Institut gemeinnützige GmbH, Frankfurt am Main (DE)

(72) Inventors: Pascal Fries, Frankfurt am Main (DE); Christopher Lewis, Frankfurt am Main (DE)

(73) Assignee: ERNST STRUNGMANN INSTITUT GEMEINNUTZIGE GMBH, Frankfurt (DE)

( * ) Notice: Subject to any disclaimer, the term of this patent is extended or adjusted under 35 U.S.C. 154(b) by 1102 days.

(21) Appl. No.: 15/313,211

(22) PCT Filed: Feb. 12, 2015

(86) PCT No.: PCT/EP2015/052944
§ 371 (c)(1),
(2) Date: Nov. 22, 2016

(87) PCT Pub. No.: WO2015/180847
PCT Pub. Date: Dec. 3, 2015

(65) Prior Publication Data
US 2017/0181707 A1    Jun. 29, 2017

(30) Foreign Application Priority Data

May 26, 2014    (EP) .................................. 14169867

(51) Int. Cl.
*A61B 5/00* (2006.01)
*A61B 17/34* (2006.01)
*A61N 1/05* (2006.01)

(52) U.S. Cl.
CPC ........ *A61B 5/6868* (2013.01); *A61B 17/3468* (2013.01); *A61N 1/0529* (2013.01);
(Continued)

(58) Field of Classification Search
CPC ... A61B 4/0478; A61B 4/6867; A61B 4/6868; A61B 2562/063; A61B 2562/066; A61B 17/3468
See application file for complete search history.

(56) References Cited

U.S. PATENT DOCUMENTS 4,800,890 A * 1/1989 Cramer ................. A61M 5/007
600/434
2006/0122676 A1 * 6/2006 Ko .................... A61M 25/0668
607/116
(Continued)

FOREIGN PATENT DOCUMENTS

| CN | 101072601 A | 11/2007 |
| WO | 2006062590 A1 | 6/2006 |
| WO | 2009125196 A1 | 10/2009 |

OTHER PUBLICATIONS

Office Action dated Apr. 11, 2019 in CN Application No. 201580027686.6.

(Continued)

*Primary Examiner* — Eun Hwa Kim
(74) *Attorney, Agent, or Firm* — Panitch Schwarze Belisario & Nadel LLP

(57) ABSTRACT

A set is provided for applying a flat, flexible two-dimensional thin-film strip into living tissue, particularly into brain tissue. The set includes the thin-film strip itself to be applied and an application tool, which is removable and mechanically connectable to the thin-film strip by a coupling device. After application of the thin-film strip in situ the application tool is removable from the tissue without residue by (Continued)

mechanically disengaging the coupling device itself, while leaving the thin-film strip behind.

16 Claims, 5 Drawing Sheets

(52) U.S. Cl.
CPC ..... *A61B 2560/063* (2013.01); *A61B 2562/04* (2013.01); *A61B 2562/164* (2013.01)

(56) References Cited

U.S. PATENT DOCUMENTS

| | | | | |
|---|---|---|---|---|
| 2008/0046056 | A1* | 2/2008 | O'Connor | A61N 1/05 607/119 |
| 2008/0089840 | A1* | 4/2008 | Shalaby | A61B 17/06166 424/9.1 |
| 2009/0125097 | A1* | 5/2009 | Bruszewski | A61B 17/3478 623/1.23 |
| 2010/0198257 | A1* | 8/2010 | Stopek | A61B 17/06166 606/228 |
| 2010/0268192 | A1* | 10/2010 | El-Hibri | A61L 29/06 604/511 |
| 2011/0224682 | A1 | 9/2011 | Westlund et al. | |
| 2011/0270361 | A1* | 11/2011 | Borsody | A61N 1/0526 607/62 |
| 2011/0301665 | A1* | 12/2011 | Mercanzini | A61B 17/34 607/45 |
| 2012/0022424 | A1* | 1/2012 | Yamamoto | A61F 9/00781 604/8 |
| 2013/0053851 | A1 | 2/2013 | Schmitz et al. | |
| 2014/0222125 | A1* | 8/2014 | Glenn | A61B 5/287 607/116 |

OTHER PUBLICATIONS

Rubehn et al., "Flexible Shaft Electrodes for Transdural Implantation and Chronic Recording", Proceedings of the 15th Annual Conference of the IFESS, 3 pgs. (2010).

Int'l Search Report and Written Opinion dated Mar. 26, 2015 in Int'l Application No. PCT/EP2015/052944.

Office Action dated Aug. 20, 2018 in CN Application No. 201580027686.6.

Office Action dated Sep. 10, 2018 in EP Application No. 15703789.6.

Office Action dated Nov. 12, 2019 in Chinese Application No. 201580027686.6 (English Translation).

* cited by examiner

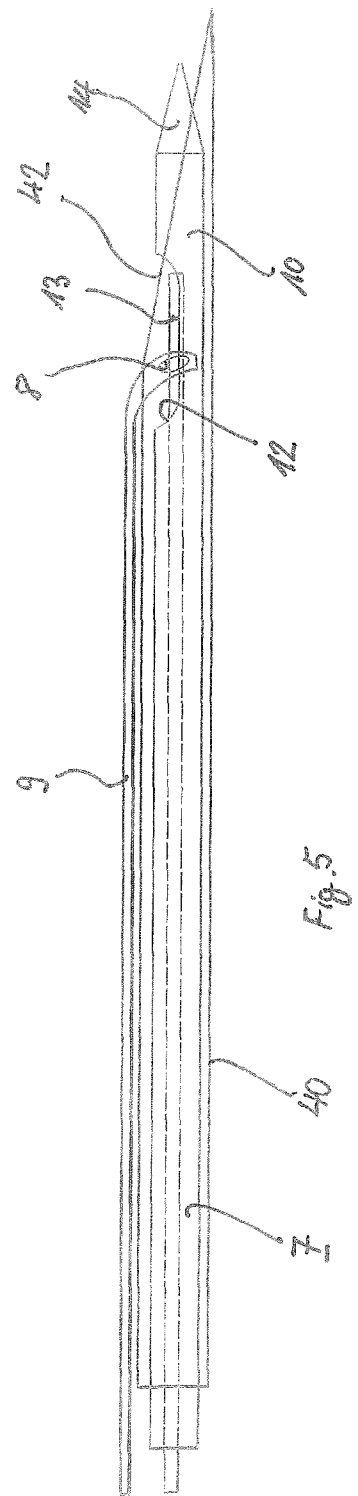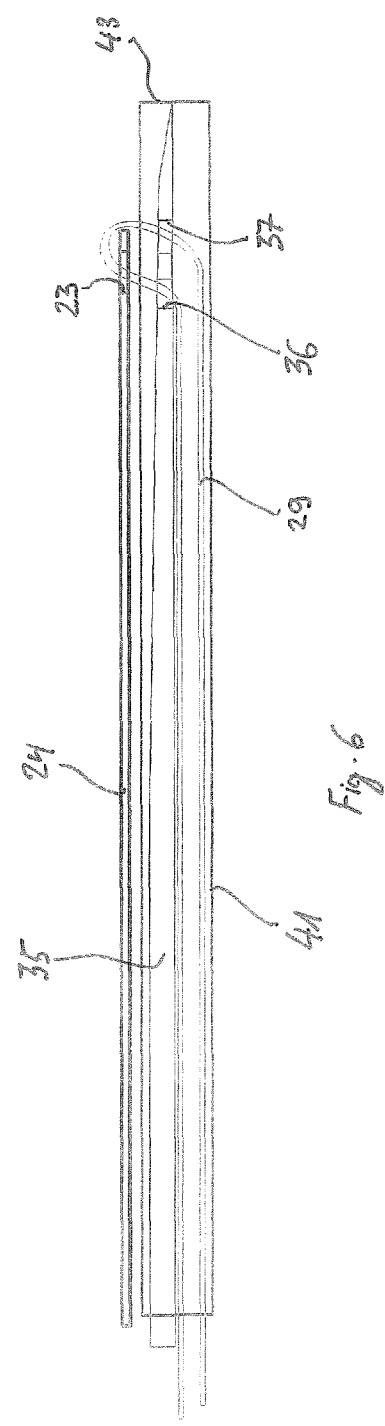

SET FOR APPLYING A FLAT, FLEXIBLE TWO-DIMENSIONAL THIN-FILM STRIP INTO LIVING TISSUE

CROSS-REFERENCE TO RELATED APPLICATIONS

This application is a Section 371 of International Application No. PCT/2015/052944, filed Feb. 12, 2015, which was published in the English language on Dec. 3, 2015, under International Publication No. WO 2015/180847 A1 and the disclosure of which is incorporated herein by reference.

BACKGROUND OF THE INVENTION

The use of sensor and effector arrays on flexible substrates is of growing relevance for biomedical applications. The ability to construct diverse devices on biocompatible substrates, which are tolerated over long time scales, will allow enhanced therapeutic and diagnostic interventions as well as improvements in brain/machine interfaces. However, it is currently difficult to implant these devices into the body in a minimally invasive way, because of their otherwise desirable flexibility.

The term thin-film strip, as used herein, indicates a strip of thin film that is flexible and therefore cannot be inserted into living tissue by itself due to mechanical barriers like the dura mater, if considering the brain as exemplified. The strip carries components that are to be deposited in the living tissue as, e. g., electronic circuits, light guides, fluid vias and the like.

Multi-electrode arrays are currently revolutionizing basic and clinical neuroscience due to their unprecedented ability to record from and stimulate in dense populations of neurons. One of the most promising technologies for fabricating multi-electrode arrays relies on the application of Micro-Electro-Mechanical Systems (MEMS) lithographic processes to realize dense arrays with arbitrary geometries on flexible, polyimide-based or parylene-based films. Such MEMS are considered as an example of flat, flexible two-dimensional thin-film strips within the scope of the present application besides others. Such techniques have been widely adopted for surface recording from the brain because they offer freedom in design, biocompatibility over long time scales, and are minimally invasive. However, many areas of the brain of especial interest for both research and clinical applications are not accessible from such surface recordings, and the targets desirable for therapeutic stimulation often lie tens of millimeters from the brain's surface. In order to achieve access to such areas, it is desirable to penetrate the brain tissue in a minimal fashion. However, current designs to achieve this goal are either macroscopic (on the order of a millimeter) or use brittle electrode substrates, such as silicon. Existing technologies thus risk unnecessary damage to the brain both during implantation, as well as in the lifetime of the implanted device.

Rubehn, B., et al. "Flexible shaft electrodes for transdural implantation and chronic recording," *Proceedings of the 15th Annual Conference of the IFESS*, Vienna (2010) propose for fulfilling the contradicting requirements of stiffness of a thin-film strip to be applied during insertion and flexibility during the course of a long-term implantation a custom insertion tool for the thin-film strips, in this case for shaft electrodes. While the shaft itself is flexible, an insertion tool is used to penetrate the dura mater. The tool comprises a tungsten rod having a diameter of 100 microns and a tapered tip, and two rods having diameters of 50 microns and blunt tips. The thicker rod is glued between the two thinner ones protruding beyond them. For the implantation it is proposed that the tapered rod slides into a U-shaped profile which is glued to the back of the shaft's tip. The whole assembly is intended to be inserted into the brain, with the tapered tip of the rod penetrating the dura mater, while the two blunt rods bear against the back of the U-profile, pushing it through the hole in the dura mater and into the tissue. Since it is attached to the U-profile, the flexible shaft is inserted into the brain matter. After placing the shaft at the right position, the tungsten insertion tool is withdrawn, leaving the micro-machined polyimide foil (the thin-film strip) and the U-profile in the brain.

The authors themselves observe that while the thin-film strip could be inserted into the cortex, it was not possible to insert it through the closed dura or pia mater. Moreover, leaving the U-profile behind in the brain can be cause for undesirable damages to the tissue.

BRIEF SUMMARY OF THE INVENTION

It is therefore the object of the present invention to propose a set for applying a flat, flexible two-dimensional thin-film strip into living tissue, in particular brain, avoiding the above mentioned drawbacks as far as possible.

The aforementioned object is achieved by a set comprising:
- the thin-film strip itself to be applied; and
- an application tool removable and exclusively mechanically connectable to the thin-film strip by a coupling device, wherein after application of the thin-film strip in the target location the application tool is removable from the tissue without residue by mechanically disengaging the coupling device itself thereby leaving the thin-film strip behind.

The benefits of such a system include:
- the ability to target deep brain structures with flexible devices that could otherwise not penetrate at all or that could not be targeted precisely;
- implantation of the thin-film strip through minimally invasive means;
- removal of the rigid implantation device without leaving any residue so that damage to brain tissue is minimized over the lifetime of the implant; and
- free determination of the timing of the insertion, i.e. the length of the penetration and the speed of release of the flexible device.

In a particular preferred embodiment, the thin-film strip is a micro-electromechanical system (MEMS) in the form of a flexible multi electrode array. The set of this embodiment of the present invention allows application of such MEMS enabling neuroscientific measurements as mentioned above.

It is preferred that the flexible thin-film strip is polyimide-based or parylene-based which is known per se in the field of the present invention.

According to one preferred embodiment the flexible thin-film strip has a reinforced retaining hole in the distal end and the application tool consists of an insertion needle having an inner bore and a window on one side next to its distal end opening towards the bore and of a retaining wire designed to pass through the inner bore of the insertion needle and through the retaining hole in the thin-film strip lying in the window during insertion of the thin-film strip into the tissue, thereby removably locking up the flexible thin-film strip to the insertion needle.

Preferably, the insertion needle is a micro-machined, surgical-grade steel tubing having an outer diameter of 200 microns and a bore of 100 microns diameter.

In a preferred embodiment the insertion needle has a conical tip (the "insertion tip") that is sharp enough (~18 degrees) to allow penetration of the dura mater and brain tissue.

Preferably, the retaining wire is a surgical grade stainless steel wire of 70 microns diameter that can pass through the bore of the insertion needle.

The insertion tool is used to insert the thin-film strip into the brain. The thin-film strip also will be referred to as the flex shaft hereinafter. For insertion, the flex shaft is coupled to the insertion needle and then released after being positioned at the target location. For coupling of the flex shaft to the insertion needle, the flex shaft is equipped with the reinforced retaining hole close to its end. This hole can have a diameter of 80 microns and aids in retaining the flex shaft on the insertion needle. The flex shaft is laid into the window on the side of the insertion needle such that the retaining hole fits precisely over the bore of the insertion needle as exposed through the window. The retaining wire is then threaded through the retaining hole and further into the tip of the insertion needle on the other end of the window. Thereby, the flex shaft is firmly attached to the insertion needle.

In order to form an abutment for the retaining wire the distal end of the insertion needle should be shut. Once the multi-electrode array has been placed in the area of interest, the retaining wire can then be removed, freeing the flex shaft, and subsequently, the insertion needle can be withdrawn without residue, leaving the flex shaft in place.

According to another preferred embodiment the flexible multi-electrode array tapers into a retaining thread next to its distal end consisting of a polyimide thread and the application tool consists of a solid insertion needle having a through bore in its distal end, the polyimide thread being designed to be threaded through the through bore in the insertion needle before applying the multi-electrode array.

In this approach, the polyimide flex shaft is coupled with the insertion needle by the polyimide thread. This technique allows for smaller dimensions of the insertion needle and sharper tips for penetrating tougher tissue. The insertion needle is preferably constructed from a 200 microns diameter steel rod. Preferably, the insertion needle is tapered in the initial 5.75 mm with a 3 degree angle and in the final millimeter to a 10 degree tip. It has a hole bored through the angled plane about 1 mm from the end The typical flex shaft for use with this insertion needle ends with a 5 cm long and 100 microns wide thread of polyimide which is narrowed further to 40 microns where it meets the flex shaft. This reduced polyimide retaining thread allows the flex shaft to be coupled to the insertion needle for implantation, but can be separated from the flex shaft mechanically once the device is implanted. The retaining thread is introduced through the hole in the insertion needle, coupling the flex shaft to the insertion needle. The flex shaft and retaining thread are produced from a single piece of polyimide and lie flush to the insertion needle. The flex shaft is inserted in this manner. Once the flex shaft has been inserted, the retaining thread is mechanically separated from the flex shaft by simply pulling on the retaining thread. The insertion needle can then be withdrawn without residue, while the flex shaft remains in place.

According to still another preferred embodiment the flexible multi-electrode array has a retaining hole next to its distal end and the application tool consists of an insertion needle having a through bore in its distal end and of a separate polyimide thread being designed to be threaded through the through bore in the insertion needle as well as through the retaining hole of the flexible multi-electrode array before applying the multi-electrode array.

In this approach, the flex shaft is coupled to the insertion needle by the polyimide thread. This embodiment is therefore a combination of the flex shaft of the first embodiment and the insertion needle of the second embodiment, the retaining wire of the first embodiment being replaced by the separate polyimide thread. The handling of this third embodiment is similar to the handling of the second embodiment. Before applying the flex shaft into the brain tissue the flex shaft is connected to the insertion needle by the separate thread by threading it through the retaining hole and through the through bore in the insertion needle. Once the flex shaft has been inserted, the polyimide thread is pulled and the mechanical connection to the flex shaft is separated such that the insertion needle and the polyimide thread can be pulled out from the surgery area without residue.

In still another preferred embodiment the flexible multi-electrode array has a reinforced retaining hole in the distal end and the application tool consists of an insertion needle having two through bores in its distal end and of a separate polyimide thread being designed to be threaded through the through bores in the insertion needle in a loop-like manner before applying the multi-electrode array, such that the through bores serve as loop thread guide.

This forth embodiment is closely related to the third embodiment as described before. The handling is also very similar except for forming the loop from the polyimide thread through the through bores in the tip of the insertion needle.

The set of the present invention and in particular all of the aforementioned embodiments can preferably be further developed by a removable guide tube which encases at least parts of the coupling device and the application tool prior to applying the assembly of application tool, coupling device and thin-film strip.

The guide tube allows for smaller diameter insertion needles and increases the precision of localization when targeting very deep structures. This is due to the additional mechanical stability of the assembly granted by the guide tube.

According to one embodiment, it is preferred that the tip of the guide tube has a sharp cannula-type cutting shape. This sharp-ended guide tube can penetrate through the tissue for some defined distance, prior to implantation of the application and the thin-film strip. This allows penetration of tough tissues and insures accurate targeting of very deep structures, for which the length of the application tool necessary to reach the target would result in potential bending of the application tool and subsequent misplacement.

According to an alternative embodiment, the tip of the guide tube can have a blunt or flat shape. The blunt-ended guide tube can be positioned against the dura mater and the application tool and the thin-film strip can be implanted through the dura mater and tissue. Again, this allows deep targets to be reached while providing stability and maintaining the structural integrity of the application tool.

Preferably, the guide tube consists of steel tube having an inner diameter of 220-260 micron and an outer diameter of 300-400 micron.

According to a very much preferred embodiment, the guide tube is provided with a channel cut into the outside thereof for the reception of the thin-film strip allowing the thin-film strip to stay on the outside of the guide tube during its insertion into the living tissue. In use, the application tool is placed inside the guide tube whereas the thin-film strip is affixed to the application tool through the channel. The channel allows the thin-film strip to remain in place later after the application tool and the guide tube have been removed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1a is a lateral view of an insertion needle;

FIG. 1b is a retaining wire;

FIG. 1c is schematic plan view of a thin-film strip in the form of a flexible multi-electrode array; and FIG. 1d is a lateral view of the assembled set, ready for use.

FIG. 2a is a lateral sectional view of an insertion needle;

FIG. 2b is a top view of the insertion needle,

FIG. 2c is a schematic plan view of a flexible multi-electrode array, tapering to a thread in its distal section; and FIG. 2d is a view of the assembled set.

FIG. 3a are sectional and top views of an insertion needle;

FIG. 3b is a schematic plan view of a flexible multi-electrode array; and

FIG. 3c is a view of the assembled set.

FIG. 4a are sectional and top views of an insertion needle;

FIG. 4b is a schematic plan view of a flexible multi-electrode array; and

FIG. 4c is a view of the assembled set.

FIG. 5 is an assembled view of the first embodiment as in FIG. 1d, completed by a guide tube having a tip with a sharp cannula-type cutting shape.

FIG. 6 is an assembled view of the fourth embodiment as in FIG. 4c, completed by a guide tube having a tip showing a blunt shape.

DETAILED DESCRIPTION OF INVENTION

Figure 1:
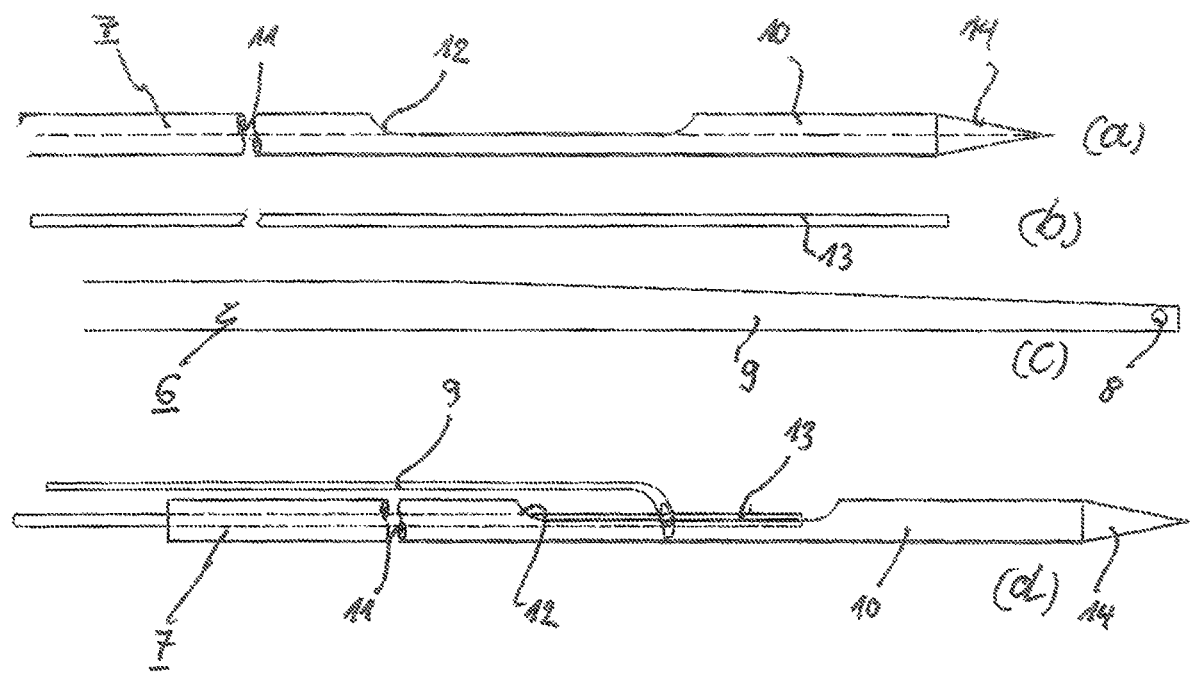
FIG. 1 are truncated longitudinal views of a set according to a first embodiment of the in in particular.

FIG. 1 shows a first embodiment of the set. It comprises three parts, namely the flex shaft 9, an insertion needle 10 as application tool 7, and a retaining wire 13.

The flex shaft 9 is shown schematically, only. It has a reinforced retaining hole 8 in its distal end. The retaining hole 8 is provided for the accommodation of the retaining wire 13 prior to and during the application of the set. The retaining wire 13 arrests the flex shaft 9 lying within a window 12 on one side of the insertion needle 10 next to its distal end to the insertion needle 10. For this purpose the window 12 opens towards the inner bore 11 of the insertion needle 10 allowing the retaining wire 13 to be threaded through the retaining hole 8 of the flex shaft 9. In this case the coupling device is formed by the retaining wire 13 in interaction with the retaining hole 8 and the insertion needle 10.

To ease the penetration of the dura mater the insertion needle 10 has a conical tip 14 at its distal end.

Figure 2:
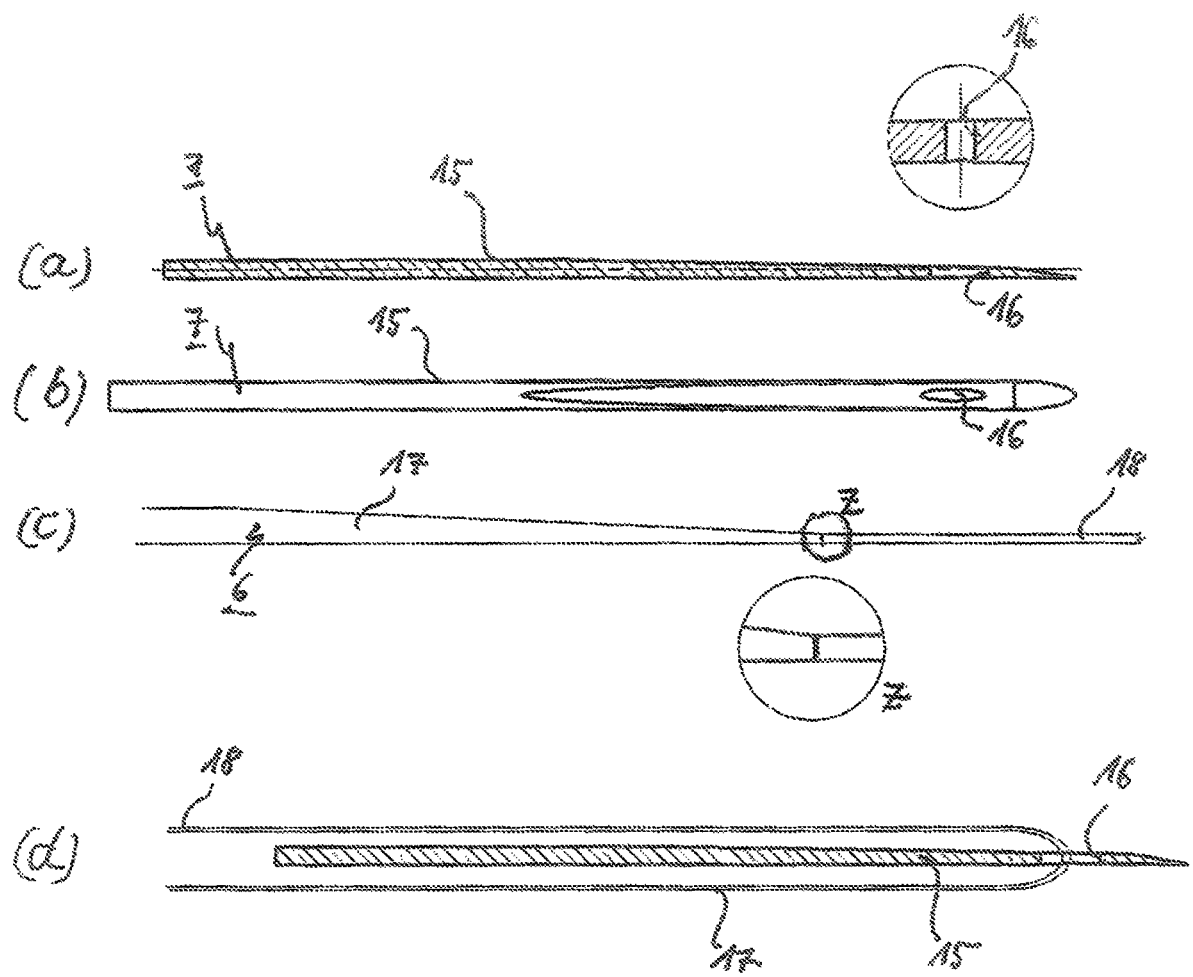
FIG. 2 are truncated longitudinal views of a set according to a second embodiment of the invention, in particular.

FIG. 2 shows an example for the second embodiment of the set. As shown, the application tool 7 consists of a solid insertion needle 15, preferably constructed from a steel rod (without an inner bore). However, it has a through bore 16 in its distal end. The through bore 16 is designed to accommodate a flexible multi-electrode array 17 or flex shaft. The flex shaft is tapering towards its distal end 18 from, for example, 100 micron to 40 micron (see detail Z) forming a polyimide thread.

Prior to use of the application tool, the set is prepared by threading the flex shaft 17 through the through bore 16 in the insertion needle 15, such that the tapered section of the flex shaft 17 is held in the area of the through bore 16. In this combination a predetermined breaking point is created for the polyimide thread of flex shaft 17. Once the flex shaft 17 has been positioned in the area of interest, the retaining thread of flex shaft 17 is separated from the flex shaft by simply pulling on its distal end 18, the retaining thread, which will lead to its breaking in the through bore 16. Then the insertion needle 15 can be pulled out from the surgery area without residue. Accordingly, the coupling device is formed by the distal end 18 of the flexible multi-electrode array 17 in interaction with the through bore 16 in the insertion needle 15.

Figure 3:
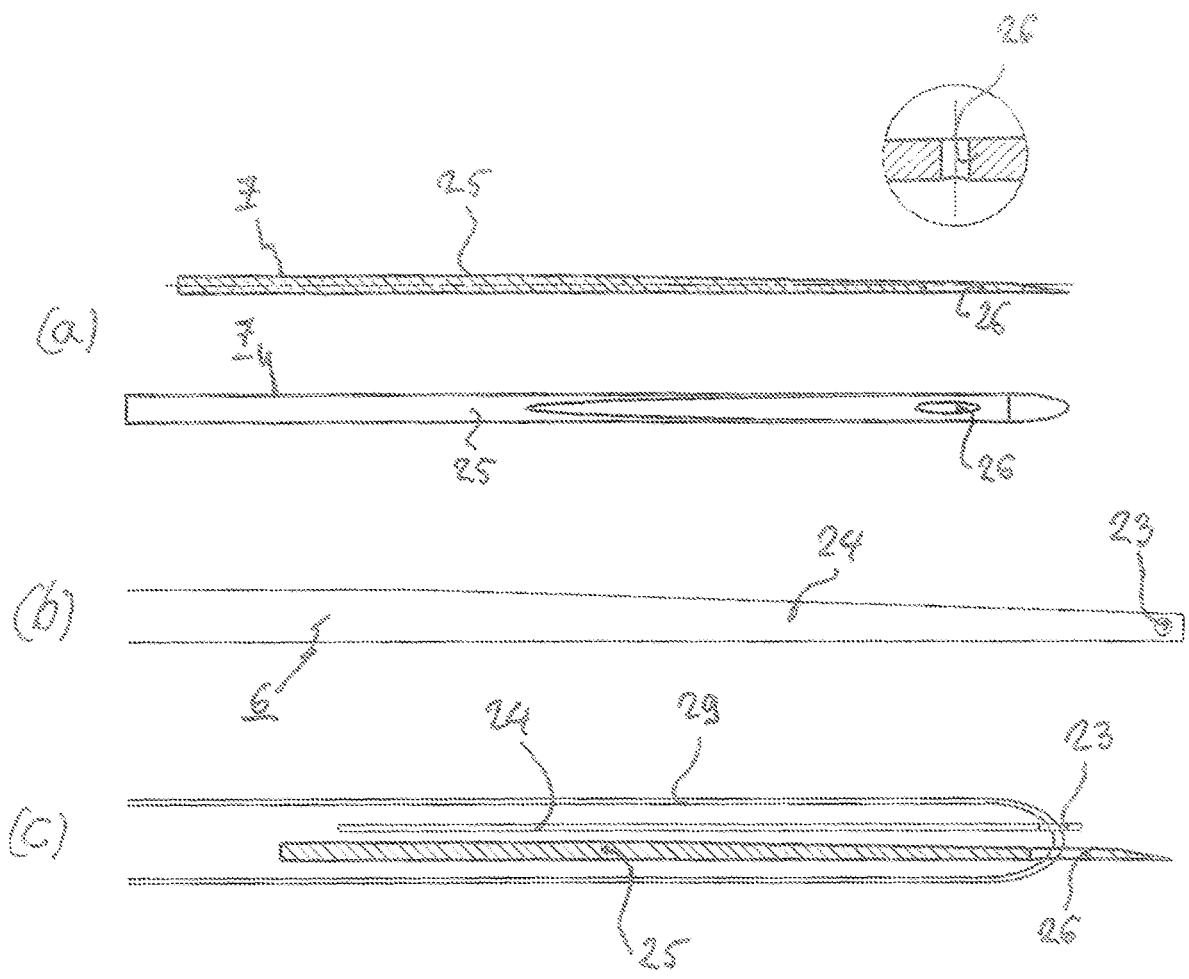
FIG. 3 are truncated longitudinal views of a set according to a third embodiment of the invention, in particular.

FIG. 3 shows a further embodiment of the set. Here, the application tool 7 consists of a solid insertion needle 25, which can be constructed similar to insertion needle 15 of the second embodiment of the set. This does mean that insertion needle 25 is preferably constructed from a steel rod having a through bore 26 in its distal end. A further component of the set in this embodiment is a separate polyimide thread 29. The polyimide thread 29 enables the releasable and exclusively mechanical connection of a flexible multi-electrode array 24 to the insertion needle 25. For this reason, the flexible multi-electrode array 24 resembles the flexible multi-electrode array 9 of the first embodiment and has a retaining hole 23 in the distal end. Now, for preparation of the application tool, the separate polyimide thread 29 is threaded through the retaining hole 23 of the flexible multi-electrode array 24 and through the through bore 26 in the insertion needle 25. The connection of the flexible multi-electrode array 24 to the insertion needle 25 during insertion of the flexible multi-electrode array 24 into a brain is tougher as compared to the connections in the other embodiments.

Once the flexible multi-electrode array 24 has reached the desired position in the tissue, the polyimide thread 29 is simply pulled on and cracks. Both ends of the cracked polyimide thread 29 as well as the insertion needle 25 can be pulled out from the surgery area leaving no residue behind. Accordingly, the coupling device in this case is formed by the polyimide thread 29 in interaction with the retaining hole 23 in the flexible multi-electrode array 24 and the through bore 26 in the insertion needle 25.

Figure 4:
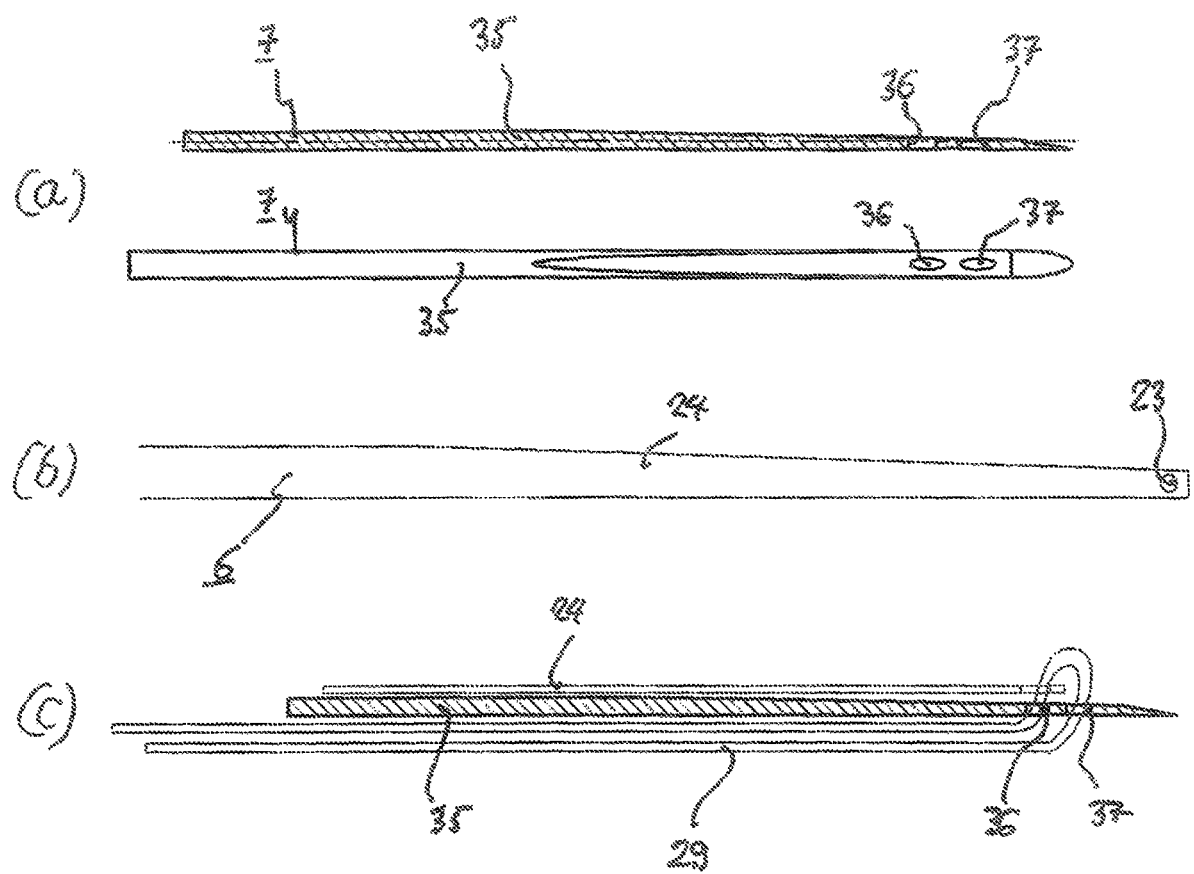
FIG. 4 are truncated longitudinal views of a set according to a fourth embodiment of the invention, in particular.

An even tougher connection between a flexible multi-electrode array and an insertion needle can be achieved by the embodiment according to FIG. 4.

This embodiment is very similar to the third embodiment. For this reason, merely the differences will be highlighted hereinafter. Apart from that reference is made to the details of the embodiment of FIG. 3.

Here, the solid insertion needle has two through bores 36, 37 in its distal end. The separate polyimide thread 29 now needs to be threaded through both through bores 36, 37, as well as through retaining hole 23 in the flexible multi-electrode array 24. The result is a very tight and robust positioning of the array allowing it to be placed into the brain even if hard dura mater needs to be passed.

The third and fourth embodiments allow reuse of the flex shaft. The flex shaft is costly and can be reused for instance in animal experiments. In contrast thereto, the flex shaft in the second embodiment needs the thin thread at the distal end 18. Once this thread has been mechanically separated, one needs to use an entirely new flex shaft with thread, since it seems impossible to fix a new thread to the already used flex shaft.

The fourth embodiment is preferably applied when it is desirable to record electric potentials from the flex shaft electrodes during its insertion into the tissue no separate thread runs over the flex shaft 24.

FIG. 5 shows the embodiment of FIG. 1d. Therefore, reference is made to the respective description. However, here the embodiment has been completed by a guide tube 40 providing enhanced mechanical stability to the set. As can be seen, the retaining wire 13 and the insertion needle 10 are placed inside the guide tube 40, whereas the flex shaft 9 is placed outside of the guide tube 40. In this embodiment the guide tube 40 has tip 42 having a sharp cannula-type cutting shape.

In FIG. 6 the embodiment of FIG. 4c is shown. For the details, reference is made to the description thereof. However, here a guide tube 41 has been added to the assembly of the other components. Clearly, the insertion needle 35 as well as the polyimide thread 29 are placed inside the guide tube 41, whereas the flexible multi-electrode array is placed outside of the guide tube 41. Here, the guide tube 41 has a tip 43 with a blunt shape.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present its invention as defined by the appended claims.

We claim:

1. A set for applying a flat, flexible two-dimensional thin-film strip at a target location into a living tissue, the set comprising:
    the thin-film strip to be applied, the thin-film strip having a thin-film strip distal end and a reinforced retaining hole in the thin-film strip distal end,
    an application tool adapted to be removably insertable into the living tissue, wherein the application tool comprises an insertion needle having an inner bore and a window on one side next to its distal end opening towards the inner bore; and
    a coupling device disposed in the application tool, the coupling device releasably attaching the thin-film strip distal end to the application tool when the thin-film strip distal end is in the application tool, the coupling device further comprises a retaining wire designed to pass through the inner bore of the insertion needle and through the retaining hole in the thin-film strip distal end;
    wherein the reinforced retaining hole in the thin-film strip distal end and the retaining wire lies in the window during insertion of the thin-film strip into the living tissue, such that the thin-film strip is removably locked to the insertion needle; and
    wherein the application tool is configured to be mechanically disengageable from the thin-film strip distal end, and is subsequently removable from the living tissue without residue thereby leaving the thin-film strip at the target location in the living tissue upon removal of the application tool.

2. The set of claim 1, wherein the thin-film strip comprises a micro-electromechanical system (MEMS) having a form of a flexible multi electrode array.

3. The set of claim 1, wherein the thin-film strip is polyimide-based or parylene-based.

4. The set of claim 1, wherein the insertion needle is a micro-machined surgical-grade steel tube having an outer diameter of 200 micron and the inner bore having a 100 micron diameter.

5. The set of claim 1, wherein the insertion needle has a conical tip which is sharp enough to allow penetration of the living tissue.

6. The set of claim 1, wherein the retaining wire is a surgical-grade stainless steel wire having a diameter of 70 micron.

7. The set of claim 1, wherein at least parts of the coupling device and the application tool are encased in a removable guide tube prior to applying the application tool, the coupling device and the thin-film strip to the living tissue.

8. The set of claim 7, wherein a tip of the guide tube has a sharp cutting shape.

9. The set of claim 7, wherein a tip of the guide tube has a blunt shape.

10. The set of claim 7, wherein the guide tube comprises a steel tube having an inner diameter of 220-260 micron and an outer diameter of 300-400 micron.

11. The set of claim 7, wherein the guide tube has a channel cut into its outside for receiving the thin-film strip, such that the thin-film strip is allowed to remain on the outside of the guide tube during its insertion into the living tissue.

12. A set for applying a flat, flexible two-dimensional thin-film strip at a target location into a living tissue, the set comprising:
    the thin-film strip to be applied, the thin-film strip tapering at its distal end into a separable polyimide retaining thread;
    an application tool is adapted to be removably insertable into the living tissue, the application tool comprising a solid insertion needle having a through bore in its distal end,
    wherein the polyimide retaining thread is threaded through the through bore in the insertion needle before applying the thin-film strip and is configured to be mechanically separable from the thin-film strip by pulling on the polyimide retaining thread, and
    wherein the application tool is configured to be mechanically disengageable from the thin-film-strip distal end and is subsequently removable from the living tissue without residue thereby leaving the thin-film strip at the target location upon removal of the application tool.

13. The set of claim 12, wherein the insertion needle comprises a 200 micron diameter steel rod.

14. The set of claim 12, wherein the insertion needle is tapered at a 3° angle in an initial 5.75 mm of the needle and is tapered to a 10° tip in a final distal millimeter of the needle.

15. A set for applying a flat, flexible two-dimensional thin-film strip at a target location into a living tissue, the set comprising:
the thin-film strip to be applied, the thin-film strip having a reinforced retaining hole in a distal end thereof; and
an application tool is adapted to be removably insertable into the living tissue,
wherein the application tool comprises a solid insertion needle having a through bore in its distal end and a separate polyimide thread designed to be threaded through the through bore in the insertion needle and through the retaining hole in the thin-film strip and the separate polyimide thread attaches the thin-film-strip distal end to the application tool before applying the thin-film strip and is configured to be mechanically separable from the thin-film strip by pulling on the retaining thread, and
wherein the application tool is configured to be mechanically disengageable from the thin-film-strip distal end and is subsequently removable from the living tissue without residue thereby leaving the thin-film strip at the target location upon removal of the application tool.

16. A set for applying a flat, flexible two-dimensional thin-film strip at a target location into a living tissue, the set comprising:
the thin-film strip to be applied, the thin-film strip having a reinforced retaining hole in a distal end thereof;
an application tool is adapted to be removably insertable into the living tissue,
wherein the application tool comprises a solid insertion needle having two through bores spaced apart longitudinally in its distal end and a separate polyimide thread threaded through the two through bores in the insertion needle in a loop shape through the retaining hole of the thin-film strip before applying the thin-film strip, such that the two through bores form a guide for the looped thread, and
wherein the application tool is configured to be mechanically disengageable from the thin-film-strip distal end and is subsequently removable from the living tissue without residue thereby leaving the thin-film strip at the target location upon removal of the application tool.

* * * * *